(12) United States Patent
Drimusz et al.

(10) Patent No.: US 8,242,792 B2
(45) Date of Patent: Aug. 14, 2012

(54) IMPEDANCE MEASUREMENT SYSTEM AND METHOD

(75) Inventors: Laszlo Otto Drimusz, Framingham, MA (US); Joseph A. Killough, Brookline, MA (US); Lee Zamir, Cambridge, MA (US)

(73) Assignee: Bose Corporation, Framingham, MA (US)

( * ) Notice: Subject to any disclaimer, the term of this patent is extended or adjusted under 35 U.S.C. 154(b) by 690 days.

(21) Appl. No.: 12/261,600

(22) Filed: Oct. 30, 2008

(65) Prior Publication Data

US 2010/0109687 A1 May 6, 2010

(51) Int. Cl.
*G01R 17/10* (2006.01)
*G01R 27/08* (2006.01)

(52) U.S. Cl. .............................. 324/725; 324/453

(58) Field of Classification Search .............. 324/452, 324/453, 725
See application file for complete search history.

(56) References Cited

U.S. PATENT DOCUMENTS

| | | | |
|---|---|---|---|
| 3,608,543 A * | 9/1971 | Longini et al. | 600/536 |
| 3,781,671 A | 12/1973 | Preikschat | |
| 4,283,675 A | 8/1981 | Sparber | |
| 4,289,035 A * | 9/1981 | Lee | 73/708 |
| 4,459,856 A | 7/1984 | Ko et al. | |
| 6,204,668 B1 * | 3/2001 | Sequeira et al. | 324/453 |
| 2007/0089988 A1 | 4/2007 | Chung et al. | |
| 2009/0105557 A1 * | 4/2009 | Najafi et al. | 600/301 |

FOREIGN PATENT DOCUMENTS

| | | |
|---|---|---|
| GB | 893907 A | 4/1962 |
| GB | 1487101 A | 9/1977 |
| WO | 2007106598 | 9/2007 |

OTHER PUBLICATIONS

Sun, Tao, et al., Digital Signal Processing Methods for Impedance Microfluidic Cytometry, Microfluid Nanofluid Research Paper, Nanoscale Systems Integration Group, School of Electronics and Computer Science, University of Southampton, Southampton S017 1BJ, UK, Springer-Verlag 2008.

Toner, Mehmet, et al., Blood-on-a-Chip, BioMEMS Resource Center, Center for Engineering in Medicine and Surgical Services, Massachusetts General Hospital, Shriners Hospital for Children, and Harvard Medical School, Boston, MA, Annu. Rev. Biomed. Eng. 2005.

Cheng, Xuanhong, et al., Lab on a Chip, A Microfluidic Device for Practical Label-free CD4+ T Cell Counting of HIV-infected Subjects, Research Paper, The Royal Society of Chemistry, 2006.

International Search Report and Written Opinion dated Dec. 23, 2009 for PCT/US2009/062387.

* cited by examiner

*Primary Examiner* — Vincent Q Nguyen

(74) *Attorney, Agent, or Firm* — Bose Corporation

(57) ABSTRACT

The impedance of ionic solutions may be determined using a bridge circuit where the ionic solution forms one leg of the bridge circuit and a reference impedance characterized by a reference time constant forms a second leg of the bridge circuit. The bridge is driven by a switched DC voltage waveform. Measurement of the ionic solution is delayed after switching to allow the reference impedance to reach its asymptotic value. The reference impedance may be varied to reduce the reference time constant.

12 Claims, 5 Drawing Sheets

IMPEDANCE MEASUREMENT SYSTEM AND METHOD

BACKGROUND

This disclosure relates to impedance measurement systems for ionic fluids.

SUMMARY

The impedance of ionic solutions may be determined using a bridge circuit where the ionic solution comprises a leg of the bridge circuit and a reference impedance characterized by a reference time constant comprises a second leg of the bridge circuit. The bridge is driven by a switched DC voltage waveform. Measurement of the ionic solution is delayed after switching to allow the reference impedance to reach its asymptotic value. The reference impedance may be varied to reduce the reference time constant.

One embodiment of the present invention is directed to a method comprising: driving a bridge circuit with a switched DC voltage, the bridge circuit having a first leg including a chamber containing an ionic solution and a second leg including a reference impedance having a non-zero imaginary portion; waiting a measurement time period after switching; measuring a chamber voltage after the measurement time period; and calculating an impedance of the ionic solution in the chamber based at least on the measured chamber voltage. In an aspect, the switched DC voltage is characterized by a switching frequency between about 200 Hz and 2000 Hz. In an aspect, the measurement time period is greater than a time constant characterizing the reference impedance in the second leg by a factor between 3 and about 10. In an aspect, the measurement time period is greater than a time constant characterizing the reference impedance in the second leg by a factor of about 5. In an aspect, the reference impedance in the second leg comprises a resistor in parallel with a capacitor. In an aspect, reference impedance in the second leg comprises a resistor in series with an inductor. In a further aspect, the reference impedance is varied to reduce the measurement time period.

Another embodiment of the present invention is directed to an impedance measurement device comprising: a fluid chamber having first and second electrodes in contact with an ionic solution contained within the chamber; a reference impedance characterized by a reference time constant; a switched DC voltage source characterized by a voltage source period, the switched DC voltage source driving a bridge circuit, the bridge circuit having a first leg including the first and second electrodes and a second leg including the reference impedance; and a controller receiving a signal corresponding to a voltage representative of the ionic solution and calculating an impedance of the ionic solution based on the received signal, wherein the controller receives the signal after a measurement time period determined by the controller. In an aspect, the reference impedance is a resistor in parallel with a capacitor. In an aspect, the reference impedance is a variable impedance controlled by the controller. In an aspect, the reference impedance is a resistor in series with an inductor. In an aspect, the reference impedance is a variable impedance controlled by the controller. In an aspect, the voltage source period corresponds to a switching frequency between 200 Hz and 2000 Hz. In an aspect, the measurement time period is greater than the reference time constant by a factor between 3 and 10. In an aspect, the measurement time period is greater than the reference time constant by a factor of about 5. In a further aspect, the controller reduces the measurement time period by varying the variable impedance.

Another embodiment of the present invention is directed to an impedance measurement device comprising: a fluid chamber having first and second electrodes in contact with an ionic solution contained within the chamber; a reference impedance characterized by a reference time constant; a switched DC voltage source characterized by a voltage source period, the switched DC voltage source driving a bridge circuit, the bridge circuit having a first leg including the first and second electrodes and a second leg including the reference impedance; and a controller receiving a signal corresponding to a voltage representative of the ionic solution and calculating an impedance of the ionic solution based on the received signal, wherein the controller receives the signal after a measurement time period, the measurement time period greater than the reference time constant. In an aspect, the reference impedance is a variable impedance controlled by the controller. In an aspect, the impedance measurement device is used in a microfluidic device.

DETAILED DESCRIPTION

Research over the past twenty five years has developed significant diagnostic and therapeutic advances in the treatment of HIV/AIDS. It has been established that counts of a specific white blood cell population, CD4+ T lymphocytes (CD4), is an important biological indicator. Regular monitoring of the CD4 counts two to four times a year is recommended for all stages of infection. A CD4 count below 200 cells/$\mu$L establishes a clinical diagnosis of AIDS and usually initiates antiretroviral treatment (ART) and other treatments against opportunistic infections. A CD4 count between about 350 and 500 cells/$\mu$L may be used as thresholds for more frequent CD4 monitoring or initiation of ART.

A CD4 count is typically determined by first collecting a blood sample by venipuncture, separating the blood cell components, labeling the target component, and imaging and counting the target component. In developed countries with modern healthcare infrastructures, the collection, preparation, and counting of the CD4 population is standard practice and diagnostic equipment have been developed to automate a portion of the CD4 count procedure. A large majority of HIV infected patients, however, live in resource-limited settings where access to blood collection by venipuncture or even the use of pipettes for any step in the diagnostic assay is problematic.

Microfluidic devices have been developed that allow resource-limited settings realistic access to at least portions of the diagnostic assay. Microfluidic devices may be characterized by the use of very small volumes of biological fluids of about 10 $\mu$L that eliminate the requirement for blood collection by venipuncture, for example. Examples of microfluidic devices are described in Cheng et. al, "A microfluidic device for practical label-free CD4+ T cell counting of HIV-infected subjects," Lab Chip, 2006, 6, pp 1-10 and in M. Toner et al., Annu. Rev. Biomed. Eng., 2005, 7, pp 77-103, herein incorporated by reference in their entirety. These microfluidic devices usually require a small sample volume typically obtainable from a simple finger prick and provide automated sample preparation and separation for the diagnostic assay. The microfluidic device typically includes a single-use disposable portion containing solutions and reagents to automatically prepare the sample, and a reusable portion including a controller and actuators to perform the sample processing. The microfluidic device is typically very portable and can be operated by a trained worker in the field as opposed to a medical facility. Counting of the separated target may be done using a light microscope or automated cell counters.

Figure 1:
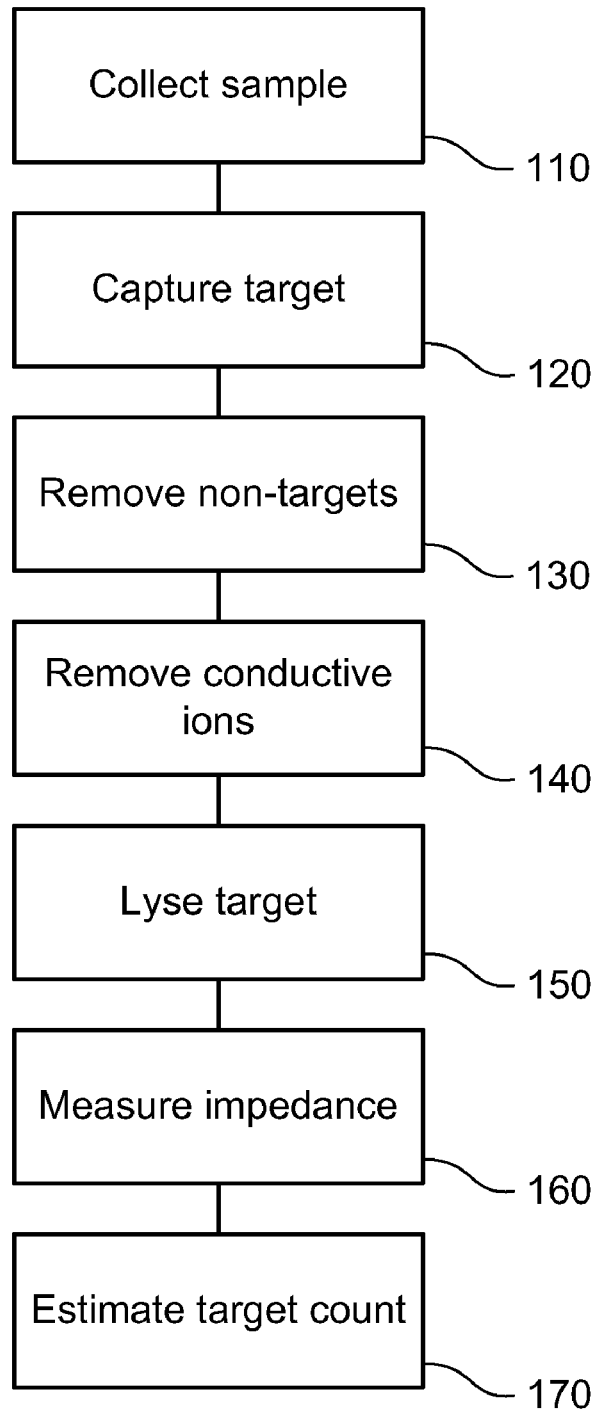
FIG. 1 is a flowchart illustrating an embodiment of the present subject matter.

FIG. 1 is a flow chart illustrating a protocol that may be used in a portable microfluidic device, also referred to as a lab-on-a-chip. For purposes of illustration, a protocol for measuring the CD4 count in a blood sample is described in the examples below but it is understood that embodiments of the present subject matter may be applied to other assays or measurement systems and modifications may readily occur to a skilled artisan based on the teachings herein and are within the scope of the described subject matter. A sample is collected at 110. For example, a simple finger prick may be used to draw about 10 µL of blood from a subject whereupon the portable device pumps the sample to a microfluidic chamber. At step 120, a target component of the blood, for example CD4 cells, is captured in a microfluidic chamber. The microfluidic chamber is typically characterized as having at least one dimension of the chamber between 1-1000 µmeters. One or more of the chamber walls is preferably coated with an antibody to capture the target cells, for example CD4 cells, in the sample. The remaining components of the sample are removed from the chamber at 130 using a wash solution, such as for example, a sterile saline or glucose solution. In some embodiments, the flow of the wash solution may be pumped at a rate slightly higher than the flow rate of the sample into the chamber. The slightly higher flow rate is believed to dislodge and remove non-target components from the chamber wall thereby increasing the fraction of target cells bound to the antibodies coating the chamber walls. For example, Published Application No. WO2007106598, published Sep. 20, 2007 describe methods and apparatus for determining appropriate shearing flow rates and are herein incorporated by reference in their entirety. At step 140, conductive ions are removed from the sample chamber by pumping a neutral solution such as, for example, an 8.5% sucrose solution through the chamber. At step 150, the bound CD4 cells are ruptured using, for example, osmotic pressure by pumping a 2% sucrose solution into the chamber. As the bound cells rupture, ions comprising the cells' cytoplasm and cellular components are released into the chamber forming an ionic solution contained by the chamber. The ionic concentration of the chamber is believed to be proportional to the number of ruptured cells. The impedance of the ionic solution in the chamber is measured at step 160 and the target count may be estimated from the measured impedance at step 170 using a predetermined correlation between impedance and CD4 cell count.

Figure 2:
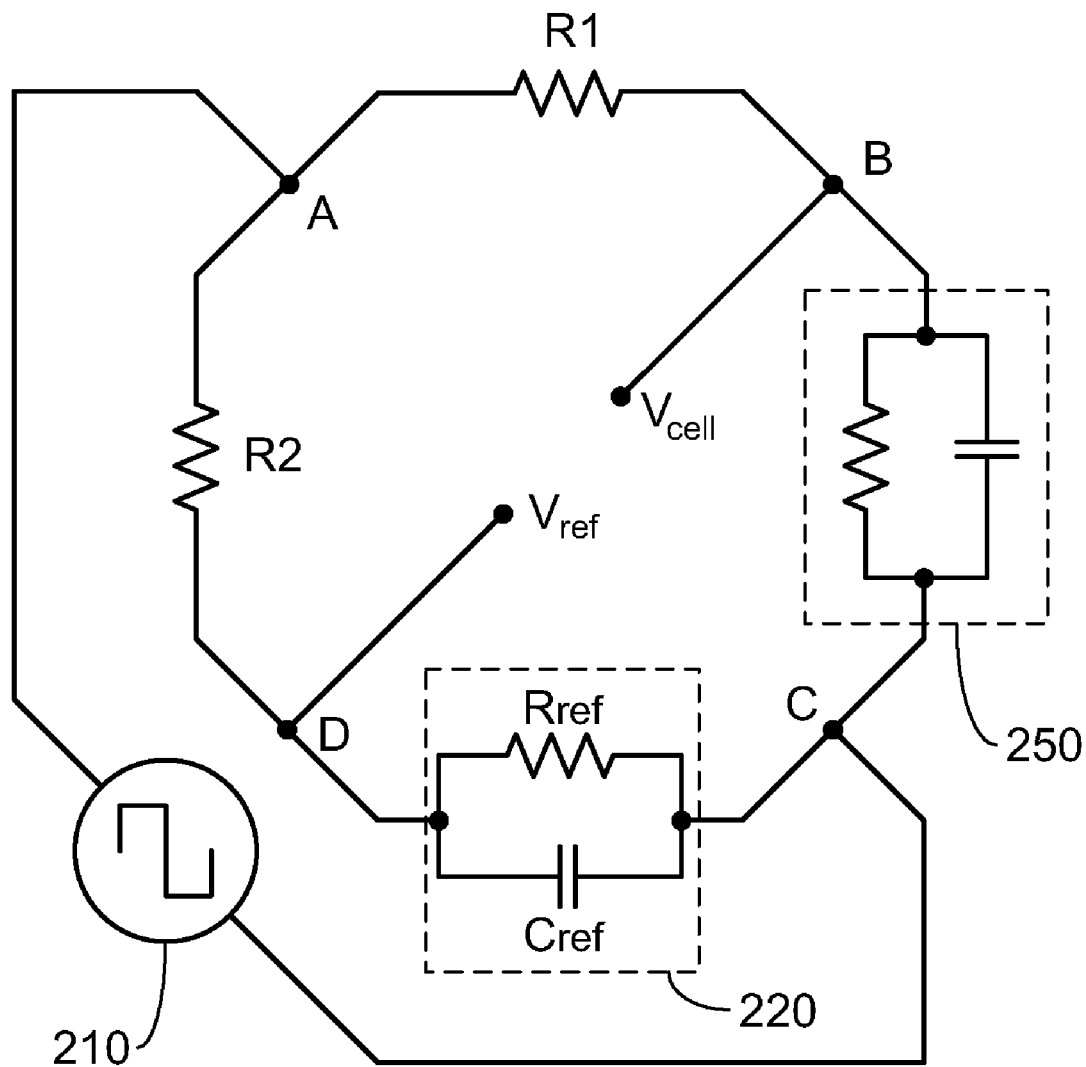
FIG. 2 is a diagram illustrating an embodiment of the present subject matter.

FIG. 2 is a diagram illustrating an embodiment for measuring the impedance of the ionic solution filling the chamber. A voltage supply 210 is applied across nodes A and C of a bridge circuit. The waveform of the voltage supply is preferably a square wave characterized by amplitudes +V and −V, herein referred to as a switched DC voltage. Resistors R1 and R2 preferably have well-characterized and precise resistance values, for example ±5%, more preferably ±2%, and more preferably ±0.1%, and may be selected such that R1=R2. A reference impedance 220 having an imaginary component is connected between nodes D and C of the bridge circuit. In the example shown in FIG. 2, the reference impedance 220 is a resistor, Rref, in parallel with a capacitor, Cref, although other combinations of resistors, capacitors, and inductors may be used as the reference impedance. The microfluidic chamber 250 includes a first electrode connected to node B and a second electrode connected to node C of the bridge circuit. In the example shown in FIG. 2, the ionic solution in the chamber 250 is modeled as a resistor, Rcell, in parallel with a capacitor, Ccell.

The example shown in FIG. 2 is similar to a Wheatstone bridge circuit except that the reference and measured resistors are replaced by components having a non-zero imaginary component in their impedance. Other types of bridge circuits may be adapted based on the teachings of the present subject matter. Examples of bridge circuits includes but are not limited to a Kelvin bridge, a Maxwell bridge, a Kelvin Varley slide, and a Kelvin double bridge.

In a typical bridge circuit, a constant DC voltage drives the circuit and a value of an unknown resistor in one of the bridge legs can be determined based on the known values of resistors in the other legs of the bridge. A DC voltage, however, cannot be used to drive the bridge circuit when the resistance of an ionic solution is desired because the ionic species in the solution will separate according to the ion's charge and change the characteristics of the ionic solution. In order to reduce the effects of charge separation, a switched DC voltage drives the bridge circuit. When using a switched DC voltage, however, the reactive characteristics of the ionic solution in the chamber induce a transient response in the bridge circuit. In a first approximation, the transient response may be characterized by a time constant that may depend on the ionic solution and the geometry of the chamber. The effect of the transient can be avoided by delaying the measurement of the cell voltage until the transient has decayed sufficiently such that the transient does not significantly contribute to the measured cell voltage. In some instances, however, the time constant characterizing the transient decay may be sufficiently large that a non-negligible amount of ion separation and electrode plating occurs resulting in an altered ionic solution. In some embodiments, the reactive characteristics of the ionic solution are balanced by an impedance, Z2, in a parallel leg of the bridge circuit. The inventors have discovered that the balancing impedance, Z2, does not have to exactly balance the impedance of the ionic solution to reduce the measurement delay period and significant benefit may be attained by selecting Z2 such that a time constant characterizing Z2 is close to the time constant characterizing the ionic solution. Although the time constant characterizing the ionic solution is not known a priori and is expected to varying depending on the cell count, a range of time constants may be estimated from reported studies and the time constant characterizing Z2 may be selected to fall within the estimated range of time constants. In some embodiments, Z2 may be varied such that the time constants characterizing Z2 and the ionic solution match. In such a situation, the measurement delay period may be significantly reduced thereby reducing the alteration of the ionic solution.

Figure 3:
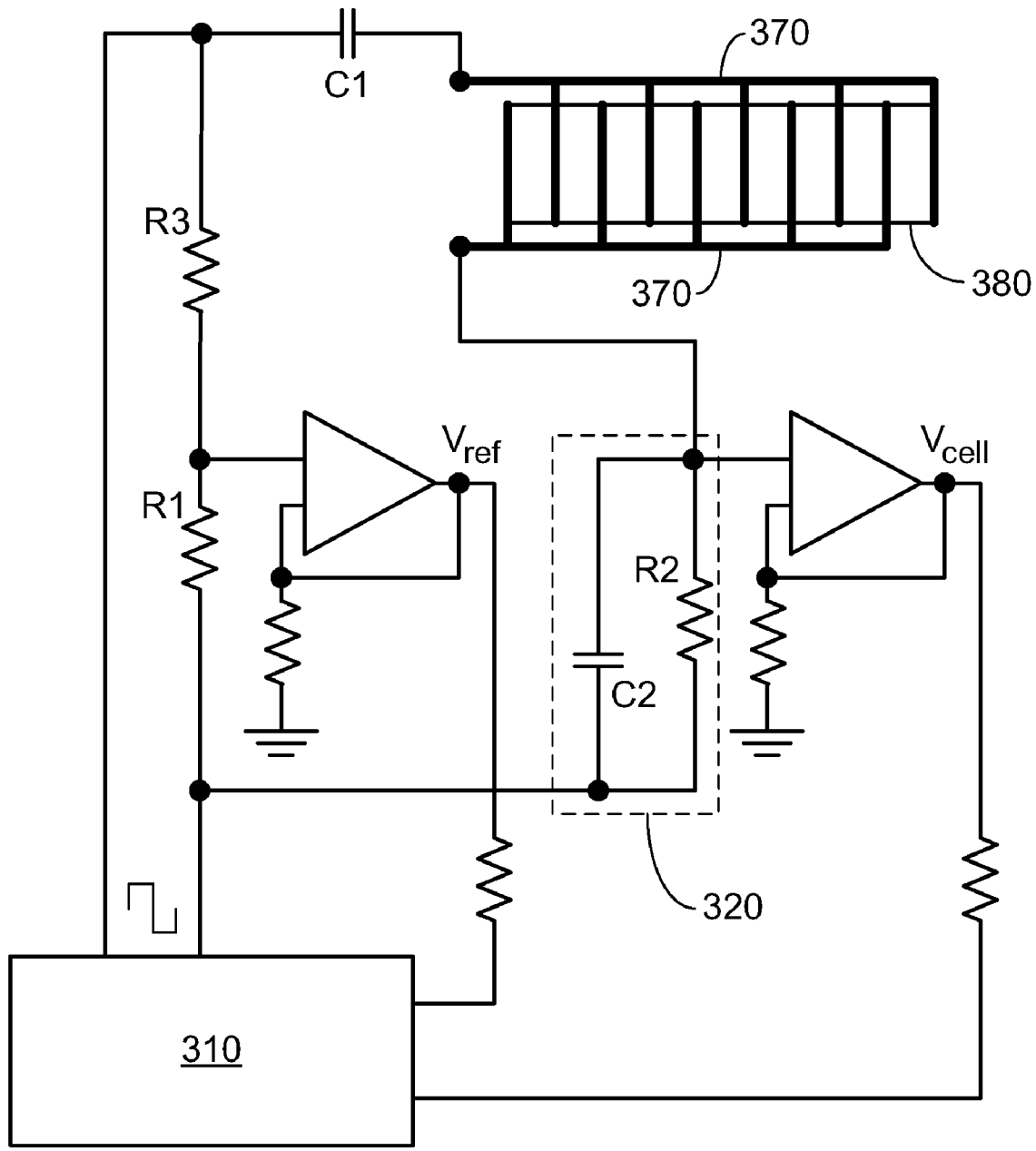
FIG. 3 is a diagram illustrating another embodiment of the present subject matter.

FIG. 3 is a diagram illustrating another embodiment of an impedance measuring device. Electrodes 370 are disposed in a microfluidic chamber 380 containing an ionic fluid. The electrodes 370 form one leg of a balanced bridge circuit with resistors R3 and R1 and impedance, Z2, 320 comprising the remaining three legs of the bridge circuit. In the example shown in FIG. 3, impedance 320 is implemented as a resistor, R2, in parallel with capacitor, C2. Impedance, Z2, may be characterized by a time constant, $\tau=R2C2$. Values of R2 and C2 may be selected such that $\tau$ is roughly equal to an expected time constant, $\tau'$, characterizing the ionic fluid. Using the example of CD4 counting, the relevant range of expected CD4 count may range from below 200 cells/μL indicating a need to start ART, through 350-500 cells/μL indicating need for increased monitoring, up to 800 cells/μL or more indicating a healthy count. A correlation between the impedance of the ionic solution corresponding to the ruptured cells and the cell count may be determined using state-of-the-art instrumentation not normally available in a field environment and the resulting correlation may be stored in a microfluidic device for use in the field. A range of expected time constants corresponding to the relevant range of CD4 counts may also be determined and the values of R2 and C2 may be selected such that $\tau$ is within the range of expected range of time constants. In other embodiments, a single time constant value corresponding to a clinically important cell threshold such as, for example, 200 cells/μL or 500 cells/μL may be used to select the values of R2 and C2.

A controller 310 drives the circuit with a switched DC square wave having amplitudes of +V and −V with a 50% duty cycle. The symmetric square wave reduces plating of the ionic species comprising the ionic fluid on the electrodes 370. An isolation capacitor, C1, prevents a DC current through the chamber 380 that may occur from an asymmetric square wave driving voltage thereby eliminating a need for a very precise driving voltage waveform. Controller 310 receives signals representing Vref and Vcell and calculates a complex impedance of the ionic solution in the chamber 380 based on Vref, Vcell, R3, R1, and Z2 using methods known to one of ordinary skill in the electronic arts. In some embodiments, controller may calculate a portion of the complex impedance of the ionic solution.

The voltage waveform driving the bridge circuit may be characterized by a cycle period, T. The cycle period, T, is selected to enable Vcell to approach an asymptotic value to within a desired accuracy after the driving voltage is switched from +V to −V or from −V to +V while reducing plating effects when the cell electrodes are held at +V or −V. The desired accuracy may be selected such that an overall uncertainty of the cell impedance is below a design value. As described above $\tau \cong \tau'$, so T may be selected such that $T \gg \tau$. As the cycle period increases, plating of ions in the ionic solution increases and may depend on the geometry of the microfluidic chamber and spacing of the chamber electrodes. In some embodiments, the cycle period may be selected to correspond to a switching frequency between 200 Hz and 2000 Hz and preferably about 1000 Hz. In a preferred embodiment, controller 310 may wait several time constants, for example 3-10$\tau$, after switching the voltage to measure Vcell and estimate the cell impedance.

Figure 4:
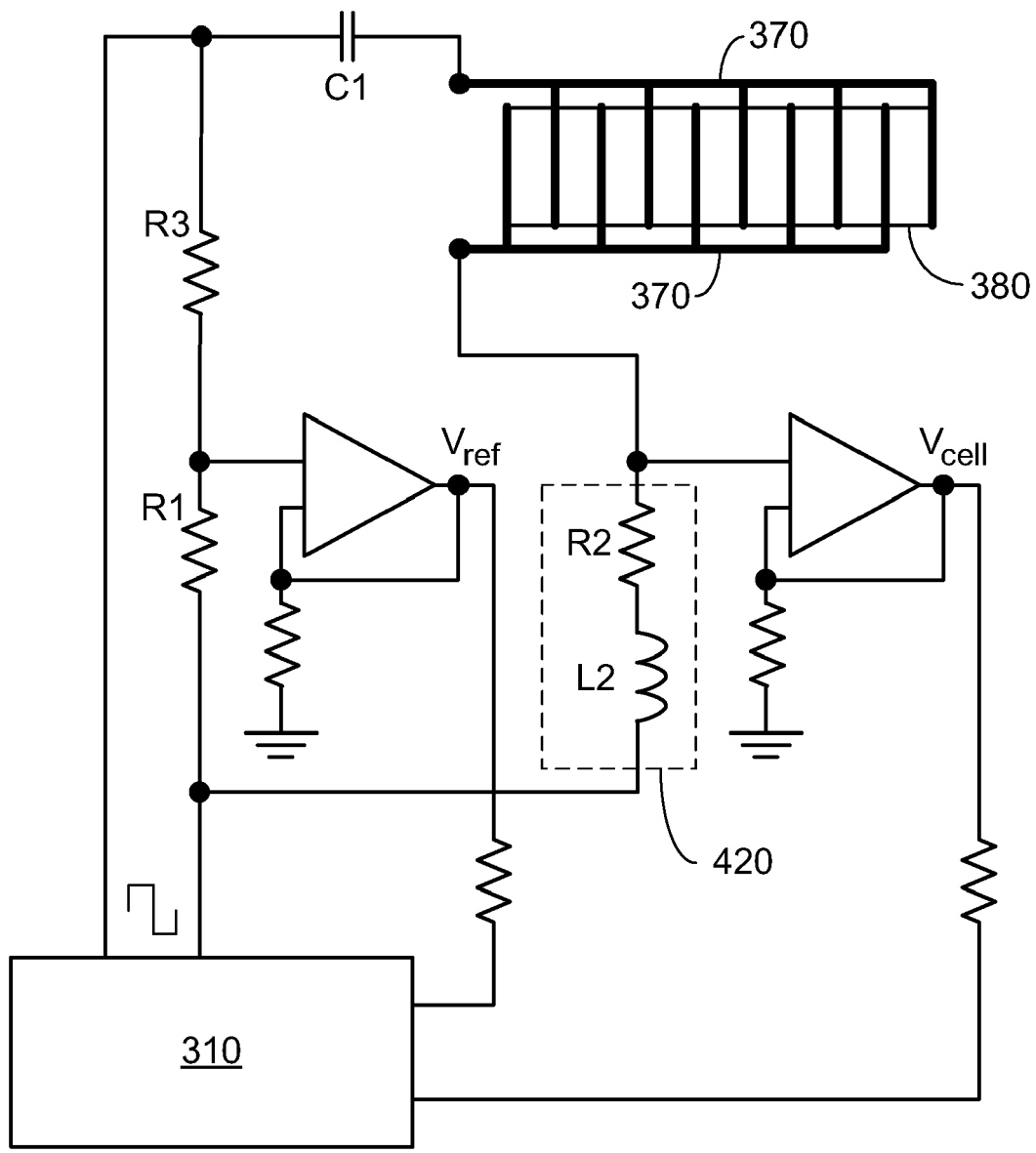
FIG. 4 is a diagram illustrating another embodiment of the present subject matter.

FIG. 4 is a diagram illustrating another embodiment of an impedance measuring device. In FIG. 4, impedance, Z2, 420 is implemented as an inductor, L2, in series with a resistor, R2.

Figure 5:
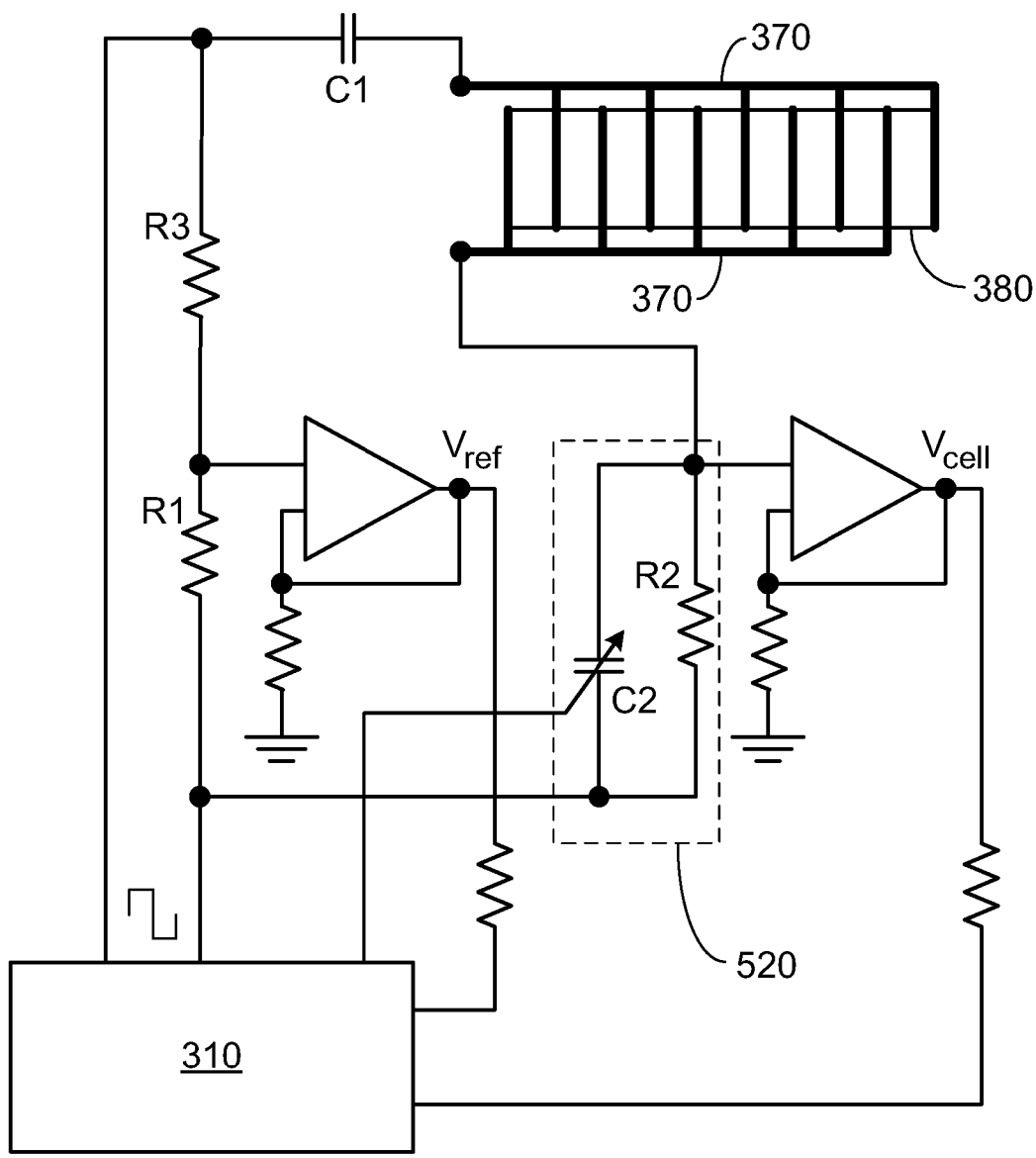
FIG. 5 is a diagram illustrating another embodiment of the present subject matter.

FIG. 5 is a diagram illustrating another embodiment of an impedance measuring device where the same reference numbers refer to similar structures. In FIG. 5, impedance, Z2, 520 includes a variable capacitor, C2, adjustable by controller 310. Controller 310 adjusts C2 to such that $\tau$ matches $\tau'$. In some embodiments, matching of the time constants is performed by controller 310 by repeatedly comparing the measured cell voltage at predetermined times and adjusting C2 until the measured cell voltage does not significantly change.

For example, the cell voltage may be measured every 0.05 T after a voltage switch. If the time constants are roughly the same, the measured cell voltage will not change between each measurement. If, for example, $\tau$ is very far from $\tau'$, each successive cell voltage will change by lesser and lesser amounts. When the controller detects a change in successive cell voltages, the controller adjusts the variable capacitor to reduce the difference in cell voltages at successive measurement times. When the cell impedance is balanced by Z2, $\tau$ can be less than the sampling frequency of controller 310 and an accurate measurement of Vcell can be made after the driving voltage is switched. In other embodiments, C2 may be held fixed and R2 varied to reduce $\tau$.

Embodiments of the systems and methods described above comprise computer components and computer-implemented steps that will be apparent to those skilled in the art. For example, it should be understood by one of skill in the art that the controller includes computer-implemented steps may be stored as computer-executable instructions on a computer-readable medium such as, for example, floppy disks, hard disks, optical disks, Flash ROMS, nonvolatile ROM, and RAM. Furthermore, it should be understood by one of skill in the art that the computer-executable instructions may be executed on a variety of processors such as, for example, microprocessors, digital signal processors, gate arrays, etc. For ease of exposition, not every step or element of the systems and methods described above is described herein as part of a computer system, but those skilled in the art will recognize that each step or element may have a corresponding computer system or software component. Such computer system and/or software components are therefore enabled by describing their corresponding steps or elements (that is, their functionality), and are within the scope of the present invention.

Having thus described at least illustrative embodiments of the invention, various modifications and improvements will readily occur to those skilled in the art and are intended to be within the scope of the invention. Accordingly, the foregoing description is by way of example only and is not intended as limiting. The invention is limited only as defined in the following claims and the equivalents thereto.

What is claimed:

1. An impedance measurement device comprising:
    a fluid chamber comprising first and second electrodes in contact with an ionic solution contained within the chamber;
    a reference impedance characterized by a reference time constant;
    a switched DC voltage source characterized by a voltage source period, the switched DC voltage source driving a bridge circuit, the bridge circuit having a first leg comprising the fluid chamber and a second leg comprising the reference impedance; and
    a controller receiving a signal corresponding to a voltage output of the bridge circuit excited by the switched DC voltage and calculating an impedance of the ionic solution based on the received signal, wherein the controller receives the signal after a measurement time period.

2. The impedance measurement device of claim 1 wherein the reference impedance is a resistor in parallel with a capacitor.

3. The impedance measurement device of claim 1 wherein the reference impedance is a variable impedance controlled by the controller.

4. The impedance measurement device of claim 1 wherein the reference impedance is a resistor in series with an inductor.

5. The impedance measurement device of claim 1 wherein the reference impedance is a variable impedance controlled by the controller.

6. The impedance measurement device of claim 1 wherein the voltage source period corresponds to a switching frequency between 200 Hz and 2000 Hz.

7. The impedance measurement device of claim 1 wherein the measurement time period is determined by the controller.

8. The impedance measurement device of claim 7 wherein the measurement time period is greater than the reference time constant by a factor between 3 and 10.

9. The impedance measurement device of claim 7 wherein the measurement time period is greater than the reference time constant by a factor of about 5.

10. The impedance measurement device of claim 7 wherein the controller reduces the measurement time period by varying the variable impedance.

11. A microfluidic device comprising the impedance measurement device of claim 1.

12. The impedance measurement device of claim 1 wherein the measurement time period is greater than the reference time constant.

* * * * *